United States Patent [19]

Mizushima et al.

[11] Patent Number: 4,647,586
[45] Date of Patent: Mar. 3, 1987

[54] PHARMACEUTICAL OIL-IN-WATER TYPE MICRO-EMULSION

[75] Inventors: Yutaka Mizushima, Tokyo; Mitsuharu Fujii, Shiga; Hiroshi Takei, Showa, all of Japan

[73] Assignee: Lederle (Japan), Ltd., Tokyo, Japan

[21] Appl. No.: 763,790

[22] Filed: Aug. 8, 1985

[30] Foreign Application Priority Data

Aug. 10, 1984 [JP] Japan ................................. 59-166612

[51] Int. Cl.⁴ .................. A61K 31/235; A61K 31/685
[52] U.S. Cl. ...................... 514/532; 514/78; 514/937; 514/938; 514/943
[58] Field of Search ................ 514/78, 937, 938, 943, 514/532

[56] References Cited

U.S. PATENT DOCUMENTS 3,169,094 2/1965 Wretlind ................................. 514/78
4,073,943 2/1978 Wretlind et al. ..................... 514/938
4,168,308 9/1979 Wretlind et al. ..................... 514/938
4,309,421 1/1982 Ghyczy et al. ........................ 514/78

Primary Examiner—Stanley J. Friedman
Attorney, Agent, or Firm—Wenderoth, Lind & Ponack

[57] ABSTRACT

A pharmaceutical oil-in-water type micro-emulsion comprising fine particles of an oil or fat containing an effective amount of a 4-biphenylylacetic acid ester of the formula

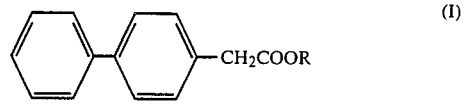

wherein R represents an alkyl group, an aqueous medium and a physiologically acceptable emulsifier for dispersing said fine particles in said aqueous medium.

This micro-emulsion is useful for treating inflammation, pain and/or fever in a mammal.

17 Claims, 7 Drawing Figures

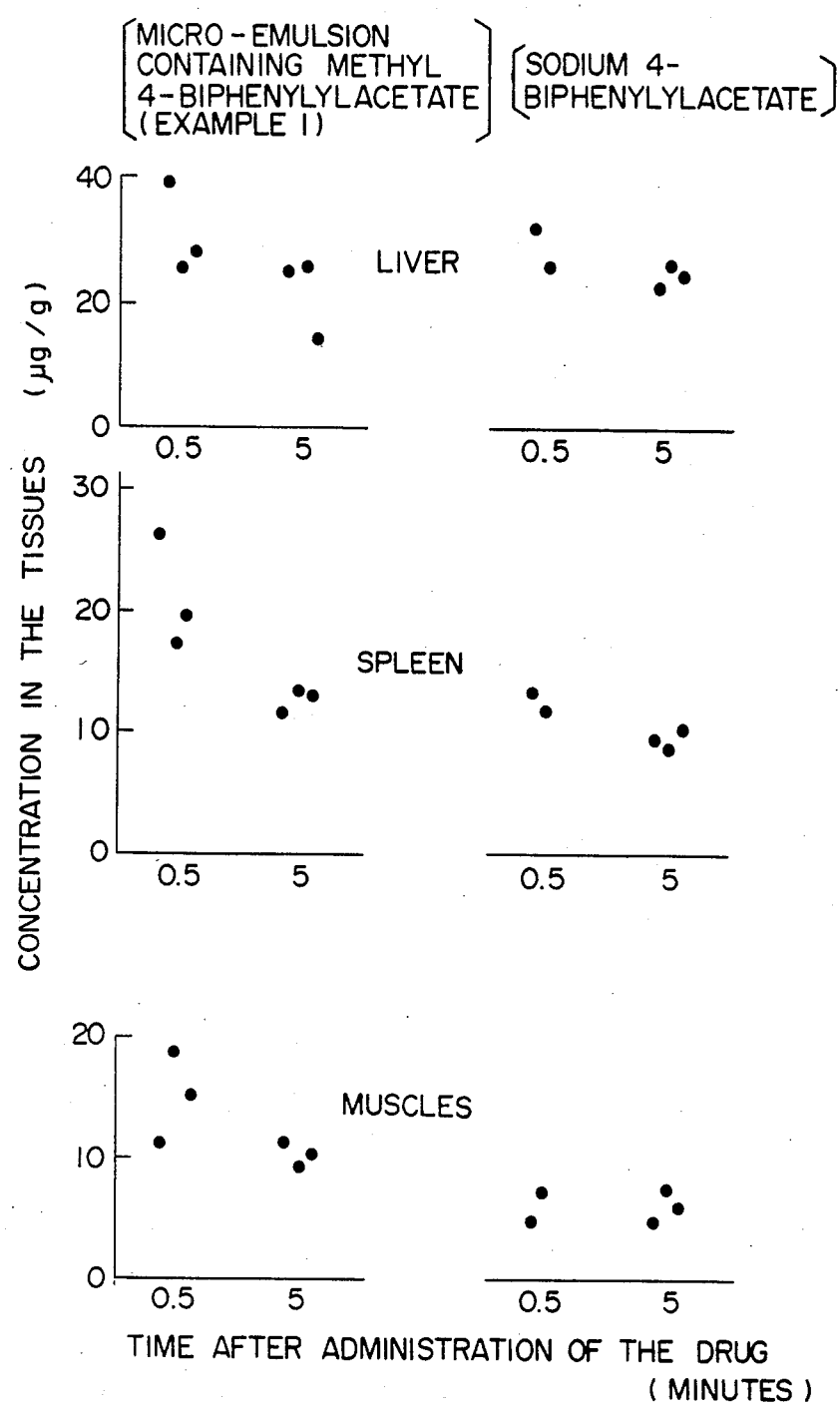

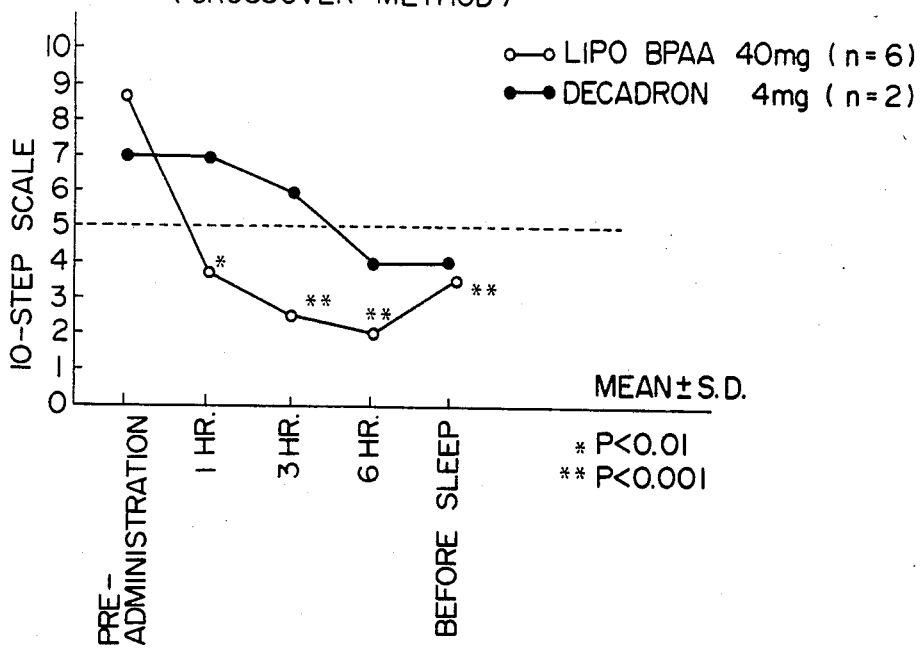
FIG. 3 ANALGESIC EFFECTS OF LIPO BPAA AND DECADRON ON VARIOUS KINDS OF NEURALGIA (CROSSOVER METHOD)
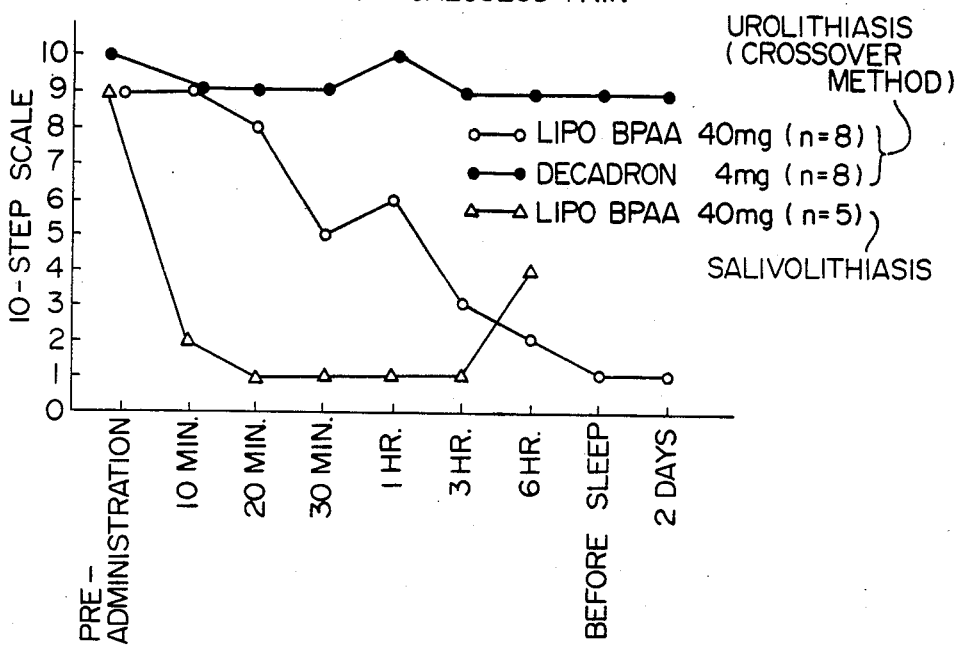
FIG. 4 ANALGESIC EFFCTS OF LIPO BPAA AND DECADRON ON CALCULUS PAIN

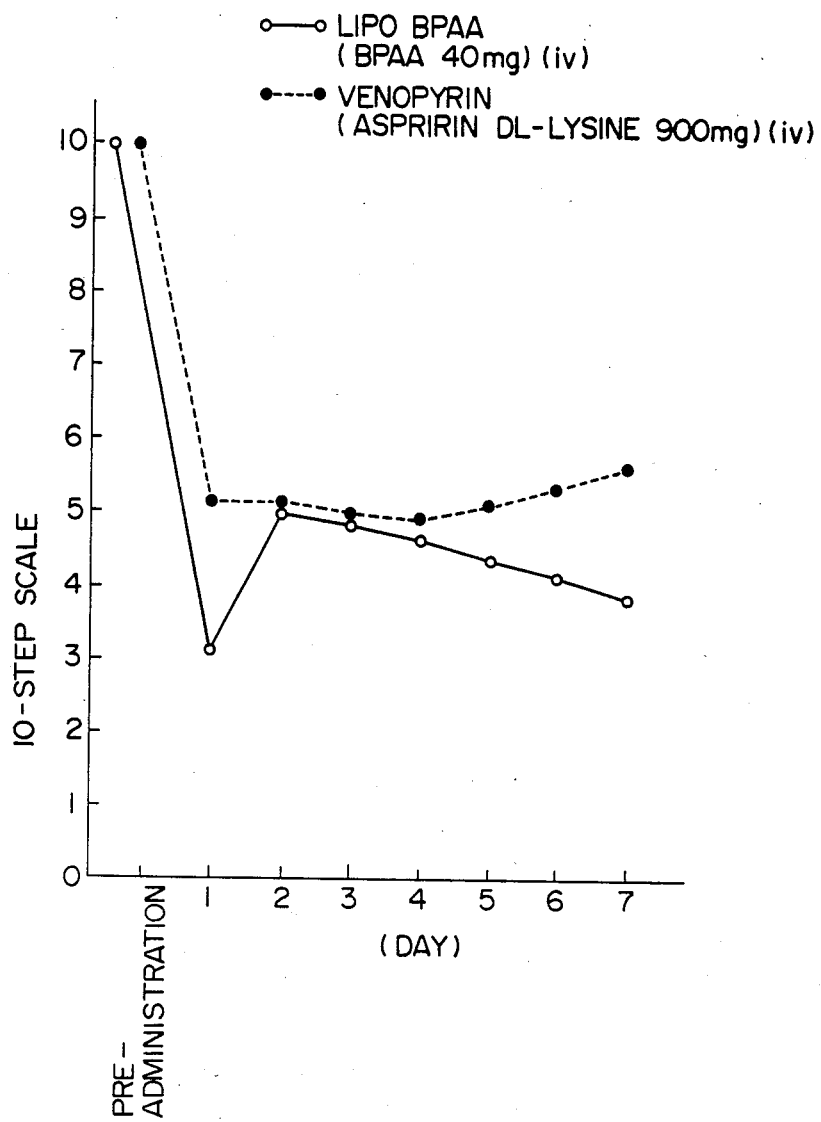

ANALGESIC EFFCT OF LIPO BPAA ON CANCEROUS PAIN

PHARMACEUTICAL OIL-IN-WATER TYPE MICRO-EMULSION

BACKGROUND OF THE INVENTION

1. Field of the Invention

This invention relates to a novel pharmaceutical composition which has excellent anti-inflammatory, analgesic and antipyretic activities and can also be administered parenterally, a method of treating inflammation, pain, and fever by using the composition, and a process for preparation of the composition.

2. Description of the Prior Art

4-Biphenylylacetic acid is a known compound having strong anti-inflammatory, analgesic and antipyretic activities (see U.S. Pat. No. 3,784,704). It is known, however, that oral or parenteral administration of 4-biphenylylacetic acid may sometimes be accompanied by ulceration or bleeding of the digestive organs. Hence, in spite of its excellent antiinflammatory, analgesic and antipyretic activities, it has not yet been used in clinical therapy as a practical drug. In order to reduce the side-effects of 4-biphenylylacetic acid while retaining its excellent pharmacological activities, 4-(4-biphenyl)-4-oxobutyric acid (common name: fenbufen; tradename NAPANOL ®, CINOPAL ®) of the following formula

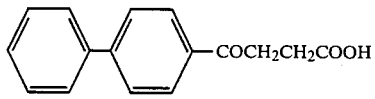—COCH$_2$CH$_2$COOH was developed on the basis of the pro-drug theory (see Arzneimittel Forschung, 30 (1), 693–746, 1980), and this compound has been widely used clinically as an orally administrable anti-inflammatory, analgesic and antipyretic agents.

Fenbufen exhibits its anti-inflammatory, analgesic and antipyretic effects after it is converted to 4-biphenylylacetic acid within the body. Metabolization to the active substance, 4-biphenylylacetic acid, requires time and its effects appear somewhat slowly.

The side-effects of fenbufen on the digestive organs are considerably reduced as compared with conventional non-steroidal anti-inflammatory agents. But it is better to use with caution when applied to patients with a history of peptic ulcer or administered in large amounts.

Recently, the targeting therapy in which a drug is administered as a dissolved form in lipid particles of a lipid emulsion has been proposed and aroused much interest. This therapy utilizes the property of lipid particles, like liposome, to be taken into the reticuloendothelial system or inflamed cells. When a lipid-soluble drug dissolved in such lipid particles is administered, the lipid particles act as a drug carrier to carry the drug selectively to a specific site where the effect of the drug is exhibited concentratingly.

As such drugs, emulsions obtained by incorporating dexamethasone palmitate, ibuprofen, flufenamic acid, indomethacine ester, prostaglandin E$_1$, and ketoprofen or its alkyl esters in lipid particles and emulsifying the lipid particles in water have been proposed [see, for example, A. Yanagawa, Japanese Journal of Inflammation, vol. 2, No. 3, Summer (1982), pages 251–257, Japanese Laid-Open Patent Publications Nos. 16818/1982, 59912/1983, 201712/1983, 222014/1983, and 13720/1984]. Among them, dexamethasone palmitate and prostaglandin E$_1$ are lipid soluble and have successfully been formed into stable lipid emulsions. They are being clinically tested for administration to humans. The other drugs do not have sufficient solubility in oils or fats such as soybean oil. Then lipid emulsions having low concentrations of drug for animal tests can be prepared from these drugs, but no stable lipid emulsion having a sufficient concentration of the active compound to produce a satisfactory clinical effect has been obtained from them. Hence, the work to develop such lipid emulsions has been suspended.

Thus, the prior art has not given sufficient results in the preparation of lipid emulsions although an excellent therapeutic effect will be expected from the administration of drugs having anti-inflammatory, analgesic and antipyretic activities as lipid emulsions. It has been strongly desired therefore to develop a drug composition which can rapidly produce effects without an impairment in anti-inflammatory, analgesic and antipyretic activities with a minimum of the aforesaid side effects.

SUMMARY OF THE INVENTION

The present invention provides a phamaceutical composition which meets the aforesaid requirements.

It is an object of this invention to provide a pharmaceutical oil-in-water type micro-emulsion comprising fine particles of an oil or fat containing an effective amount of a 4-biphenylylacetic acid ester of the formula

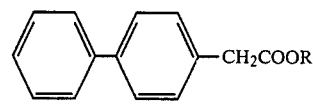—CH$_2$COOR (I)

wherein R represents an alkyl group, an aqueous medium and a physiologically acceptable emulsifier for dispersing said fine particles in said aqueous medium.

Another object of this invention is to provide a method of treating inflammation, pain and/or fever in a mammal, which comprises parenterally administering the aforesaid pharmaceutical oil-in-water type micro-emulsion to the mammal.

Still another object of this invention is to provide a process for preparing the aforesaid pharmaceutical oil-in-water type micro-emulsion, which comprises dissolving an effective amount of the 4-biphenylylacetic acid ester of formula I in oil or fat optionally under heat, adding a predetermined amount of an emulsifier and as required other additives such as an emulsifying aid as required, a stabilizer and an isotonizing agent, stirring the mixture under heat to form a uniform mixture, adding water, then treating the mixture by a homogenizer to prepare a crude oil-in-water type emulsion, and thereafter homogenizing the crude emulsion by a high-energy homogenizer under high pressure.

The 4-biphenylylacetic acid ester of formula I used in this invention has a strong affinity for, and are well miscible with, oils or fats such as soybean oil, and form stable micro-emulsion containing the 4-biphenylylacetic acid ester in clinically effective concentrations. When the resulting micro-emulsion containing the 4-biphenylylacetic acid ester is administered to a mammal, it exhibits much stronger anti-inflammatory, analgesic and antipyretic activities than when the 4- biphenylylacetic acid itself is administered in solution or suspension forms. Moreover, its side effects such as disturbance in the digestive organs are drastically reduced, and its high activities appear rapidly and last over an extended period of time.

Accordingly, since the 4-biphenylylacetic acid ester of formula (I) has better compatibility with oils or fats, the micro-emulsion of this invention has greater stability than the lipid emulsion of 4-biphenylylacetic acid itself. The 4-biphenylylacetic acid ester of formula (I) dissolved in lipid particles is distributed efficiently to a site of inflammation and hydrolyzed in situ by the action of esterase to 4-biphenylylacetic acid, the active substance, and consequently exhibits its excellent effects.

The emulsion of the present invention is a systemically administrable micro-emulsion which has enabled 4-biphenylylacetic acid to be used in clinical therapy for the first time. It is a valuable preparation which greatly contributes to the medical field, especially in the therapy of inflammation, pain and fever.

BRIEF DESCRIPTION OF THE DRAWINGS

FIG. 2 is a graph showing the results of measuring the distribution of the micro-emulsion of the invention to the tissues; and FIGS. 3 to 7 are graphs showing the results of clinical tests of the micro-emulsion of this invention.

DETAILED DESCRIPTION OF THE INVENTION

Figure 1:
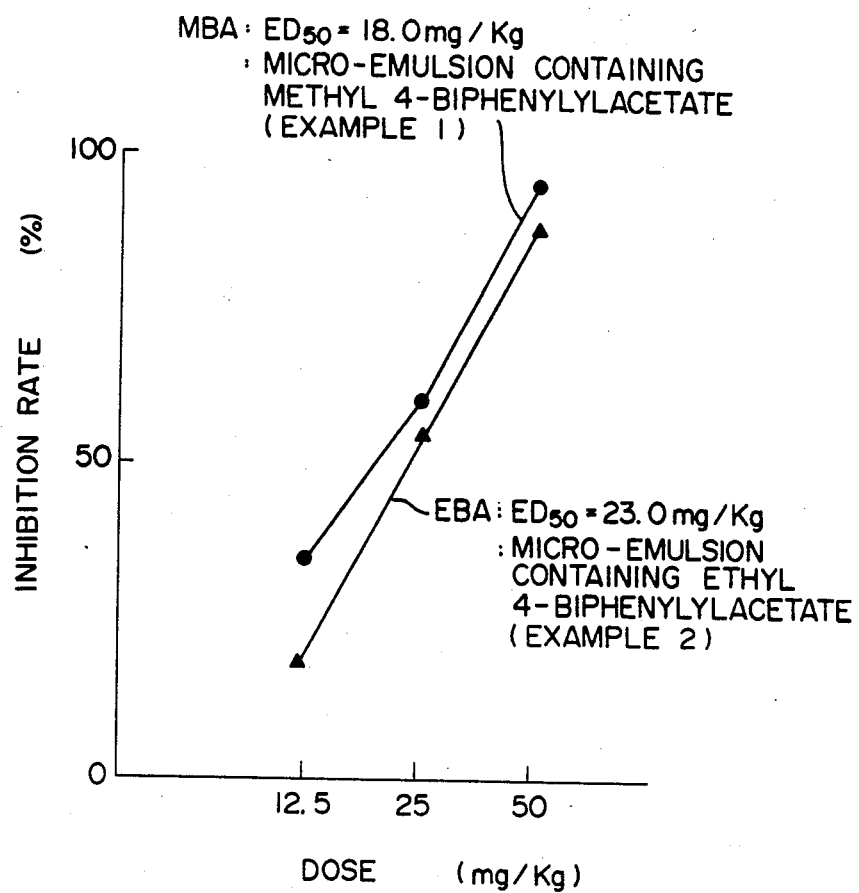
FIG. 1 is a graph showing the results of measuring the analgesic activity of the micro-emulsion of the present invention.

Of the 4-biphenylylacetic acid esters of formula (I), those having high lipophilicity are preferred in this invention.

In formula (I) representing the 4-biphenylylacetic acid ester, R represents alkyl groups, for example alkyl groups having 1 to 18 carbon atoms such as methyl, ethyl, n-propyl, isopropyl, n-butyl, isobutyl, sec-butyl, tert-butyl, n-pentyl, isoamyl, n-pentyl, n-hexyl, octyl, nonyl, decyl, dodecyl, tetradecyl, hexadecyl and octadecyl. Lower alkyl groups such as methyl and ethyl are preferred, and the ethyl group is most preferred.

The term "lower", used in the present specification, means that a group or compound qualified by this term has not more than 6, preferably not more than 4, carbon atoms.

It is presumed that the 4-biphenylylacetic acid ester exhibits its pharmacological effect when converted to 4-biphenylylacetic acid in vivo by the enzymatic action of esterase.

The pharmaceutical micro-emulsion of this invention is prepared by introducing the compound of formula (I) into particles of an oil or fat used in the preparation of ordinary lipid emulsions. For example, it can be easily prepared by dissolving the compound of formula (I) in fine particles of the oil or fat, and dispersing the fine particles in water using an emulsifier to form an oil-in-water emulsion.

The oil or fat which can be used in preparing the pharmaceutical micro-emulsion of this invention includes any pharmaceutically acceptable oil and fat which are normally used. Specific examples include vegetable oils such as soybean oil, cottonseed oil, rapeseed oil and safflower oil; triglycerides of medium-chain fatty acids having 8 to 12 carbon atoms (such as caprylic acid, capric acid and lauric acid), normally abbreviated as MCT; and mono- or di-glycrides of fatty acids having 6 to 18 carbon atoms (such as caproic acid, capric acid, myristic acid, palmitic acid, linoleic acid and stearic acid). They may be used either singly or in combination. Among them, vegetable oils and Panacet 810 (MCT mixture, a product of Nippon Oils and Fats Co., Ltd.) are preferably used, and pharmaceutically acceptable soybean oil fitting the standards of medicines stipulated in Japanese Pharmacopoeia is most preferred. The amount of such an oil or fat is not strictly limited, and can be varied widely depending upon the type or amount of the pharmacologically effective compound of formula (I) and/or the other ingredients. Generally, it is 1 to 50% (w/v), preferably 3 to 30% (w/v), more preferably 5 to 20% (w/v).

Unless otherwise stated, all percentages "% (w/v)" used to denote the contents or amounts used of the ingredients of the pharmacetucial micro-emulsion in the present specification and the appended claims mean parts by weight per 100 parts by volume of the final pharmaceutical micro-emulsion.

The emulsifier used to disperse the fine particles of the oil or fat stably in an aqueous medium may be at least one compound selected from physiologically acceptable phospholipids and nonionic surface-active agents, preferably the physiologically acceptable phospholipids. Examples of the physiologically acceptable phospholipids include yolk phospholipid, vegetable oil phospholipids such as soybean phospholipid, and phosphatidyl choline. Examples of the nonionic surface-active agents include polyoxyalkylene copolymers (for example, polyoxyethylene-polyoxypropylene copolymers having an average molecular weight of 1,000 to 20,000), and hydrogenated castor oil polyoxyalkylene derivatives [such as hydrogenated castor oil polyoxyethylene-(40)-ether and hydrogenated castor oil polyoxyethylene-(20)-ether]. These emulsifiers can be used either singly or in combination. Preferably, the emulsifiers used in this invention generally have an HLB of 6 to 15, preferably 10 to 14. Among the above emulsifiers, yolk phospholipid and vegetable phospholipids such as soybean phospholipid are preferred. The vegetable oil phospholipids, particularly purified soybean phospholipid, are most suitable because they have a better emulsifying power and can form more uniform, finer and more stable phospholipid particles than the yolk phospholipid. Desirably, the vegetable oil phospholipids are purified to such an extent that the phosphatidyl choline content reaches at least 50% by weight, preferably at least 80% by weight. The soybean oil phospholipid so purified may have an iodine value of generally 30 to 50, preferably about 40.

The emulsifier is used in an amount sufficient to disperse the oil or fat particles containing the 4-biphenylylacetic acid ester in an aqueous medium and maintain them stably in it. Depending upon the type of the emulsifier, its amount is generally 0.05 to 25% (w/v), preferably 0.2 to 6% (w/v), more preferably 0.6 to 2.4% (w/v). On the basis of the oil or fat, the suitable amount of the emulsifier is 6 to 24 parts by weight, especially 6 to 15 parts by weight, per 100 parts by weight of the oil or fat.

In the micro-emulsion of the present invention, a moderate amount of distilled water or deionized water may be used as the aqueous dispersion medium. If required, a small amount of a pharma eutically acceptable water-miscible organic solvent such as ethanol may be incorporated.

As required, an isotonizing agent and other additives such as an emulsification aid and a stabilizer may further be incorporated in the micro-emulsion of the present ivnention.

Examples of the isotonizing agent include glycerol, sugar alcohols such as sorbitol and xylitol; monosaccharides such as glucose and fructose; disaccharides such as maltose; and amino acids such as L-alanine, L-valine and glycine. Of these, glycerol is especially suitable.

The isotonizing agent is added to adjust the osmotic pressure of the micro-emulsion to a value nearly equal to that of a body fluid. The amount of the isotonizing agent is such that its final concentration in the micro-emulsion is 0.1 to 0.5 mole/liter, preferably 0.25 to 0.35 mole/liter. More specifically, it can be incorporated usually in the following proportions depending upon the type of the isotonizing agent.

| | Proportions, % (w/v) | | |
|---|---|---|---|
| Isotonizing agent | General range | Preferred range | Most preferred range |
| Glycerol | 2–4 | 2–3 | about 2.5 |
| Sugar alcohol | 2–6 | 2.5–5 | 3–4 |
| Monosaccharide | 4–6 | 4.5–5.5 | about 5 |
| Disaccharide | 8–12 | 9–11 | about 10 |
| Amino acid | 3–5 | 3–4 | about 3.5 |

Examples of the emulsifying aid that can be incorporatted include fatty acids having 10 to 20 carbon atoms (such as stearic acid, palmitic acid, linoleic acid and linolenic acid) and salts thereof (such as sodium and potassium salts), phosphatidyl ethanolamine, phosphatidyl serine and stearylamine. It may be used generally in an amount of up to 0.4% (w/v), preferably 0.01 to 0.2% (w/v). In particular, the fatty acid or its salt can be advantageously used in an amount of 0.01 to 0.1% (w/v), and phosphatidyl ethanolamine, phosphatidyl serine and stearylamine may be advanageously used in an amount of 0.05 to 0.3% (w/v), especially 0.1 to 0.2% (w/v).

Cholesterol or tocopherol, for example, may be used as a stabilizer. Conveniently, cholesterol may be used generally in an amount of up to 1.2% (w/v), preferably 0.2 to 0.4% (w/v), and tocopherol may conveniently be used in an amount of up to 2.5% (w/v), preferably 0.2 to 0.8% (w/v).

Albumin, its fatty acid amide derivatives, and polysaccharides or their fatty acid ester derivatives may also be used as the stabilizer. From the standpoint of antigenicity, albumin is desirably one derived from a human when preparing a pharmaceutical micro-emulsion for humans. The fatty acid amide derivatives thereof may, for example, be compounds obtained by amidating 5 to 40% of the entire amino groups present in albumin with fatty acids having 14 to 18 carbon atoms (such as palmitic acid and stearic acid). Examples of the polysaccharides include dextran, pullulan and hydroxyethyl starch. The fatty acid ester derivatives of these polysaccharides may be compounds obtained by, for example, esterifying 5 to 40% of the entire hydroxyl groups present in the polysaccharides with fatty acids having 14 to 18 carbon atoms such as palmitic acid and stearic acid. The stabilizer may be added generally in an amount of 0.02 to 5% (w/v), preferably 0.2 to 2.5% (w/v).

The micro-emulsion of this invention may be prepared by using emulsifying methods known per se. Ordinary homogenizers may be used as an emulsifying machine. To prepare a stable lipid micro-emulsion, it is convenient to use two types of homogenizer. Specifically, the micro-emulsion of this invention may be prepared by dissolving an effective amount of the 4-biphenylylacetic acid ester in the oil or fat such as pharmaceutically acceptable soybean oil optionally under heat, adding a predetermined amount of an emulsifier such as refined soybean phospholipid and as required an isotonizing agent and other additives such as an emulsification aid or a stabilizer, stirring the mixture under heat to make a uniform mixture, adding water, and treating the mixture in a homogenizer to prepare a crude emulsion of the oil-in-water type, and thereafter, homogenizing the crude emulsion by a pressurized homogenizer such as Gaulin high-energy homogenizer. The stabilizer and the isotonizing agent may be added to the resutling micro-emulsion.

Desirably, the above emulsifying operation is carried out generally until the dispersed oil or fat particles in the resulting emulsion have a mean particle diameter of not more than about 1 micron, preferably not more than 0.3 micron, more preferably 0.1 to 0.15 micron.

The 4-biphenylylacetic acid ester of formula (I) as a pharmacologically active ingredient is conveniently used so that its concentration generally becomes 0.01 to 50% (w/v), preferably 0.01 to 10% (w/v), more preferably 1 to 5% (w/v).

As required, the micro-emulsion of this invention so prepared may be lyophilized. The powder obtained by lyophilization can be converted back to the original micro-emulsion when it is dissolved in water. It should be understood that the term "micro-emulsion", as used in the present application, also denotes such a lyophilized form of the micro-emulsion.

Thus, according to one preferred embodiment of this invention, there is provided a pharmaceutical oil-in-water type micro-emulsion consisting essentially of 5 to 50% (w/v) of fine particles of an oil or fat containing 0.01 to 10% (w/v) of the 4-biphenylylacetic acid ester of formula (I), 0.05 to 25% (w/v) of a physiologically acceptable emulsifier, an isotonizing agent in an amount sufficient to isotonize the emulsion, a water.

According to a more preferred embodiment of this invention, there is provided a pharmaceutical oil-in-water micro-emulsion consisting essentially of 5 to 30% (w/v) of fine particles of soybean oil having dissolved therein 1 to 5% (w/v) of ethyl 4-biphenylylacetate, 0.5 to 2.5% (w/v) of purified soybean oil phospholipid, 1 to 4% (w/v) of glycerol, and the remainder being water.

The micro-emulsion of this invention containing the 4-biphenylylacetic acid ester has excellent transferability to a site of inflammation (incorporation in inflamed cells) when administered parenterally by injection, for example. As a result, the pharmacologically effective compound exhibits its pharmacological effect strongly and concentratedly at the the site of inflammation for an extended period of time. In ddition, its side effects and toxicity on the digestive organs are very little. The micro-emulsion has excellent stability and is very useful as an anti-inflammatory, analgesic and antipyretic agent.

The excelent pharmacological effets, low toxicity and high stability of the micro-emulsion of this invention are demonstrated by the following experiments.

[A]Pharmacological tests

A-1: Effect of inhibiting carrageenin-induced paw edema

[Test 1]

(a) Experimental animals: Wistar strain male rats (body weight 160–220 g), 7 per group.

(b) Test drugs:

The emulsion containing methyl 4-biphenylylacetate or ethyl 4-biphenylylacetate in a concentration of 2% (w/v), calculated as 4-biphenylylacetic acid prepared by Example 1 or 2 given hereinafter was diluted to 40, 80, and 160 times, with physiological saline, and each of the solutions was administered at a dose of 10 ml per kg of the animal. As a control drug, an aqueous solution of sodium 4-biphenylylacetate was used.

(c) Experimental procedure:

The volume of the left hind paw of each rat was measured with a plethysmometer (supplied by Ugo Basile Company). A 1% carrageenin solution as an inflammation inducer was injected subcutaneously into the left hind paw of each rat to induce paw edema. The volume of the paw of the rat was measured before the administration of carrageenin and every hour after the administration up to 6 hours. The test drug was used in three doses of 1.25 mg/kg, 2.5 mg/kg, and 5.0 mg/kg. Sodium 4-biphenylylacetate as a control drug was used in two doses of 2.5 mg/kg and 5.0 mg/kg. The test drugs were intravenously administered 2 hours after the injection of carrageenin. The edema inhibition rate were calculated by the following equation.

$$\text{Edema inhibition rate } (\%) = \frac{Ec - Et}{Ec} \times 100$$

Ec: the volume of edema of the control group to which only the solvent was administered at each time (average value)

Et: the volume of edema in the drug-administered group at each time (average value)

(d) Experimental Results:

The results are shown in Table 1.

The micro-emulsion of this invention containing methyl 4-biphenylylacetate showed a signifcant edema inhibitive effect at any of the doses from 1 hour after the administration of the drug. Its activity lasted until 4 hours after the administration of the drug (6 hours after carrageenin administration). Likewise, the micro-emulsion of this invention containing ethyl 4-biphenylylacetate showed a significant edema inhibitive effect at doses of 2.5 mg/kg and 5.0 mg/kg from 2 hours after the administration of the drug and its effect was long-lasting. On the other hand, sodium 4-biphenylylacetate as a control drug showed a less effect than that of the above micro-emulsion. On the basis of these experimental results, the 20% edema inhibitory effect ($ED_{20}$) at 2 hours after administration was calculated from the dose-response curve. It was found that the micro-emulsions of this invention containing methyl 4-biphenylylacetate and ethyl 4-biphenylylacetate respectively showed about 6 and about 3 times as strong an effect as the control sodium 4-biphenylylacetate.

TABLE 1

| | | | Effects on Carrageenin-induced Paw Edema in Rats [Test 1] | | | | | |
| --- | --- | --- | --- | --- | --- | --- | --- | --- |
| | | | Edema inhibitory effect (inhibition rate, %) | | | | | |
| Drug | Dose (mg/kg) | Number of animals | 2 hours[b] | 3 hours | 4 hours | 5 hours | 6 hours | $ED_{20}$ (mg/kg) |
| Micro-emulsion containing methyl 4-biphenylylacetate | 1.25 | 7 | 1.8 | 18.9*[c] | 21.7** | 24.6** | 18.4** | 1.25 |
| | 2.5 | 7 | 1.8 | 18.9* | 24.6** | 24.6** | 23.4** | |
| | 5.0 | 7 | 3.6 | 28.0** | 34.8** | 41.5** | 35.0** | |
| Micro-emulsion containing ethyl 4-biphenylylacetate | 1.25 | 7 | 2.2 | 3.3 | 8.7 | 11.9 | 9.9 | 3.0 |
| | 2.5 | 7 | 2.2 | 4.9 | 19.1* | 28.8** | 18.4* | |
| | 5.0 | 7 | 2.2 | 8.2 | 23.5** | 30.6** | 27.9** | |
| Sodium 4-biphenylylacetate | 2.5 | 7 | 0 | 8.4 | 13.2 | 17.1 | 19.8 | 8.5 |
| | 5.0 | 7 | 0 | 9.5 | 15.1 | 17.4 | 20.8 | |

[a]Calculated as 4-biphenylylacetic acid
[b]Times after injection of carrageenin (the drug was administered 2 hours after the injection of carrageenin)
[c]Statistically analyzed figures against the solvent control group. *$p < 0.05$, **$p < 0.001$

[Test 2]

(a) Experimental animals: SD-strain male rats (120–180 g).

(b) Test Drugs:

A micro-emulsion containing ethyl 4-biphenylylacetate prepared as in Examples 11, 12, 13 and 14 given hereinafter was administered at a dose of 5 ml per kg of the animals. Venolipid ® (Morishita Pharmaceutical Co., Ltd.) was used as a vehicle control. As control drugs, a solution or suspension of ethyl 4-biphenylylacetate in physiological saline containing 0.5% Cremophor EL ® (Sigma Chemical Company, a solubilizing agent), 0.2% of polyethylene glycol 400 and 10% of dimethyl sulfoxide, a physiological saline solution of sodium 4-biphenylylacetate and a physiological saline solution of Aspirin DL-lysine [Venopirin ®, Green Cross Co.] were used. As the vehicle control of the control drugs, the above solvents were used.

(c) Experimental procedure:

A 1% carrageenin solution in physiological saline was injected subcutaneously in an amount of 0.05 ml into the planter surface of the left hind paw of each rat via a 25 gauge needle fitted to a 0.25 ml syringe. One hour after carrageenin injection, the rats were randomized on the basis of the edema volume, and intravenous administration of the drugs and vehicles followed immediately. The volume of the left hind paw was measured by a plethysmometer (Ugo Basile) prior to the injection of the carrageenin solution and at 2, 3, 4, 5 and 6 hours after the carrageenin injection. As the volume of edema, an increase in the paw volume was taken.

The inhibition percents were calculated in accordance with the same calculation formula as in Test 1.

(d) Experimental results

The micro-emulsion of this invention in intravenous injection showed an excellent anti-inflammatory activity against the carrageenin-induced paw edema in a dose range of 1.25 to 10.0 mg/kg, calculated as 4-biphenylylacetic acid. The $ED_{30}$ value was 4.2 mg/kg, calculated as 4-biphenylylacetic acid. In contrast, the physiological saline solution of ethyl or sodium 4-biphenylylacetate, which is different from the micro-emulsion of this invention, showed an anti-inflammatory effect in a dose range of 2.5 to 10.0 mg/kg, calculated as 4-biphenylylacetic acid, but its $ED_{30}$ was 15.8 and 10.5 mg/kg.

It can be found that the micro-emulsion of this invention shows two to three times as strong an effect as the ordinary solution form.

(d) Experimental results:
The results are shown in Table 3 below. The edema at the left hind paw injected with the adjuvant was signifi-

TABLE 2

Effects on Carrageenin-induced Paw Edema in Rats [Test 2]

| Test drugs | Dose[a] (mg/kg) | No. of Animals | Inhibition (%) Time after Carrageenin Injection | | | | | $ED_{30}$[b] (mg/kg) |
|---|---|---|---|---|---|---|---|---|
| | | | $2^h$ | $3^h$ | $4^h$ | $5^h$ | $6^h$ | |
| Micro-emulsion | 1.25 | 7 | 12.7*[c] | 17.5* | 13.7 | 12.0 | 14.0 | 4.2 |
| of ethyl 4- | 2.5 | 7 | 25.5** | 36.8** | 39.2** | 40.0** | 31.9** | |
| biphenylyl- | 5.0 | 7 | 25.5** | 31.6** | 31.4** | 36.0** | 27.7** | |
| acetate | 10.0 | 7 | 30.9** | 36.8** | 39.2** | 40.0** | 31.9** | |
| Ethyl 4- | 1.25 | 7 | 14.0 | 17.5 | 9.6 | 9.8 | 6.4 | 15.8 |
| biphenylyl- | 2.5 | 7 | 19.3* | 26.3** | 17.3** | 17.6* | 12.8 | |
| acetate | 5.0 | 7 | 17.5* | 28.1** | 23.1** | 23.5** | 19.1 | |
| | 10.0 | 7 | 22.8* | 22.8* | 26.9** | 25.5* | 27.7** | |
| Sodium 4- | 1.25 | 7 | 6.6 | 0 | 8.5 | 5.2 | 6.1 | 10.5 |
| biphenylyl- | 2.5 | 7 | 19,7 | 11.7 | 18.6** | 20.7* | 10.2 | |
| acetate | 5.0 | 6 | 9.8 | 6.6 | 20.3** | 19.0** | 30.6** | |
| | 10.0 | 7 | 23.0* | 28.3* | 35.6** | 29.3** | 30.6** | |
| Aspirin- | 50 | 7 | 24.2 | 26.7* | 35.7* | 29.6* | 30.0* | 81.6 |
| DL.Lysine | 100 | 7 | 24.2* | 26.7* | 26.8 | 22.2 | 20.0 | |
| | 200 | 7 | 37.9** | 43.3** | 50.0** | 42.6** | 44.0** | |

[a]Doses of the micro-emulsion of ethyl 4-biphenylylacetate, ethyl 4-biphenylylacetate and sodium 4-biphenylylacetate are expressed as those of 4-biphenylylacetic acid, and doses of aspirin DL-lysine as those of aspirin.
[b]Dose required to cause a 30% inhibition of edema volume against the vehicle control. This value was calculated from the mean % inhibition of swelling combined for measurement intervals indicated.
[c]*P < 0.05, **p < 0.01

A-2. Inhibitory activity of adjuvant-induced arthritis [Test 1]
(a) Experimental animals: CRJ-CD(SD)-strain female rats (5 to 7 weeks old), 6 per group.
(b) Test drugs:

Micro-emulsions containing methyl 4-biphenylylacetate and ethyl 4-biphenylylacetate in a concentration of 2% (w/v) calculated as 4-biphenylylacetic acid (prepared as in Examples 1 and 2 below) were diluted with Venolipid ® (Morishita Pharmaceutical Co., Ltd.) to 20 40 and 80 times, and administered at a dose of 10 ml per kg of the animals. Venolipid was used as the vehicle control.

(c) Experimental procedure:
A suspension containing 0.6 mg of heated dead cells of *Mycobacterium butyricum* in liquid paraffin as an adjuvant was injected into the left hind paw of each rat. Each of the test drugs was administered into the tail vein for 5 days starting from the 15th to 19th day after the injection of the adjuvant. The volume of the hind paw was measured by a plethysmometer (supplied by Ugo Basile Company) at the specified times till the 25th day after the injection of the adjuvant. The edema inhibition rate was calculated in accordance with the same calculation formula as in [Test 1] of A-1.

cantly inhibited by the intravenous administration of the micro-emulsions containing methyl 4-biphenylylacetate and ethyl 4-biphenylylacetate respectively in each of the doses, and the inhibitory action showed dose-dependence.

TABLE 3

Effects on Adjuvant-induced Polyarthritis in Rats - Changes in the Adjuvant-induced Paw [Test 1]

| Drugs | Dose[a] (mg/kg) | Number of animals | Volume of the paw injected with adjuvant (inhibition %) | | | | | | |
|---|---|---|---|---|---|---|---|---|---|
| | | | 15th day[b] | 16th day | 17th day | 18th day | 19th day | 22nd day | 25th day |
| Solvent control group | 0 | 6 | 3.36 | 3.51 | 3.49 | 3.29 | 3.46 | 3.72 | 3.33 |
| Micro-emulsion containing methyl 4-biphenylyl-acetate | 2.5 | 6 | 3.33 | 3.20 (8.8) | 2.91 (16.6) | 2.87 (12.8) | 2.79*[c] (19.4) | 3.00* (19.4) | 3.02 (9.3) |
| | 5.0 | 6 | 3.32 | 3.02 (14.0) | 2.93 (16.0) | 2.69* (18.2) | 2.56** (26.0) | 3.04* (18.3) | 3.08 (7.5) |
| | 10.0 | 6 | 3.35 | 3.26 (7.1) | 3.02 (13.5) | 2.76 (16.1) | 2.58** (25.4) | 3.05 (18.0) | 3.31 (0.6) |
| Micro-emulsion containing ethyl 4-biphenylyl-acetate | 2.5 | 6 | 3.36 | 3.23 (8.0) | 3.17 (9.2) | 3.05 (7.3) | 2.97 (14.2) | 3.45 (7.3) | 3.36 (−0.9) |
| | 5.0 | 6 | 3.35 | 3.23 (8.0) | 2.98 (14.6) | 2.81 (14.6) | 2.70* (23.0) | 3.16 (15.1) | 3.28 (1.5) |
| | 10.0 | 6 | 3.27 | 2.87 (18.2) | 2.89 (17.2) | 2.83 (14.0) | 2.64* (23.7) | 2.98* (19.9) | 3.34 (−0.3) |

[a]Calculated as 4-biphenylylacetic acid.
[b]Days after injection of the injection (each test drug was intravenously administered for 5 days from the 15th to the 19th day.)
[c]Statistically analyzed figures against the solvent control group. *p < 0.05, **p < 0.01

[Test 2]
(a) Experimental animals: SD-strain famale rats 140–180g).
(b) Test drugs: The same as in A-1 [Test 2].
(c) Experimental procedure:
Rats were anesthetized with ether inhalation, and 0.6 mg of *Mycobacterium butyricum* suspended in 0.1 ml of white paraffin oil was immediately injected intradermally into the planter surface of the left hind paw of each rat via a 27 gauge needle fitted to a 0.5 ml syringe (day 0). On the 14th day after the adjuvant injection, arthritis-established rats selected by development of secondary lesions were used. Volumes of both hind paws in arthritis-established rats were measured by a plethysmometer (UGO BASILE), and the rats were randomized on the basis of the edema volume in the adjuvant-injected paw. Once daily, beginning on the 14th day up to the 18th day, drugs and vehicles were administered intravenously. Measurements of both paw volumes were performed every day from the 15th day up to the 18th day, and on the 21st day and the 24th day. The inhibition percent were calculated in accordance with the calculation formula as in [Test 1] of A-1.

(d) Experimental results

The micro-emulsions of this invention showed an excellent anti-inflammatory action on adjuvant-induced arthritis in rats in intravenous administration in doses of 1.25 to 10.0 mg/kg calculafted as 4-biphenylylacetic acid.

The $ED_{20}$ was 5.8 mg/kg calculated as 4-biphenylylacetic acid.

In contrast, when ethyl or sodium 4-biphenylylacetate was administered as an ordinary solution, its $ED_{20}$ was 14.5 and 14.3 mg/kg, respectively, calculated as 4-biphenylylacetic acid.

Accordingly, the micro-emulsion of this invention has about 3 times as great an effect as an ordinary solution form of the active compound.

A-4: Effects on reversal of abnormal 3-legged gait in rats (analgesic activity)

(a) Experimental animals: SD-strain male rats (120-165 g).

(b) Test drugs: The same as in A-1 [Test 2].

(c) Experimental procedure:

A 40% suspension of dried brewers yeast in physiological saline was injected (0.25 ml/rat) subcutaneously into the planter surface of the left hind paw of each rat. Three hours later, the walking gait on a wire mesh platform was assessed for each rat.

| Gist scoring system: |
| --- |
| Score of; 0 = Normal gait in the presence of a severely inflamed paw. There is continuous use of the inflamed foot pad. |
| 0.5 = As above, with intermittent mild limping. |
| 1.0 = Constant limping, but continuous use of |

TABLE 4

Effects on Adjuvant-induced Polyarthritis in Rats - Changes in the Adjuvant-injected Paw [Test 2]

| Test drugs | Dose[a] (mg/kg) | No. of Animals | Inhibition (%) Days after Adjuvant Injection | | | | | | $ED_{20}$[b] (mg/kg) |
| --- | --- | --- | --- | --- | --- | --- | --- | --- | --- |
| | | | 15 | 16 | 17 | 18 | 21 | 24 | |
| Micro-emulsion | 1.25 | 8 | 9.1 | 10.3 | 16.4*[c] | 13.2 | 6.2 | 9.3 | 5.8 |
| of ethyl 4- | 2.5 | 8 | 11.6 | 14.6 | 17.6* | 16.1* | 5.7 | 9.9 | |
| biphenylyl- | 5.0 | 8 | 14.9 | 16.0* | 25.8** | 23.5** | 18.7* | 18.1 | |
| acetate | 10.0 | 8 | 21.3** | 23.4* | 30.9** | 27.9** | 16.4 | 19.0 | |
| Ethyl 4- | 1.25 | 8 | −8.0 | −5.1 | −3.3 | −4.6 | −19.2 | −23.2 | 14.5 |
| biphenylyl- | 2.5 | 8 | −3.7 | 0 | 6.7 | 5.8 | −6.5 | −17.5 | |
| acetate | 5.0 | 8 | 5.6 | 7.2 | 15.5 | 15.0 | 8.9 | 1.3 | |
| | 10.0 | 8 | 2.8 | 10.7 | 15.2 | 15.6 | 3.0 | −9.8 | |
| Sodium 4- | 1.25 | 7 | −1.8 | 1.2 | 7.9 | 3.9 | −7.5 | −14.1* | 14.3 |
| biphenylyl- | 2.5 | 8 | −4.2 | 1.5 | 1.9 | −3.9 | −15.7 | −29.7** | |
| acetate | 5.0 | 8 | 7.3 | 12.9 | 17.9 | 15.6 | 9.2 | 2.8 | |
| | 10.0 | 8 | 8.2 | 9.5 | 17.9 | 16.6 | 1.3 | −0.7 | |
| Aspirin- | 50 | 8 | −2.7 | −5.2 | −3.8 | −2.6 | −12.4 | −20.0** | 320.5 |
| DL.Lysine | 100 | 8 | 4.0 | 9.2 | 13.2 | 6.8 | 4.2 | −2.8 | |
| | 200 | 7 | 6.7 | 11.3 | 16.4 | 15.3 | 7.2 | 6.2 | |

[a]Doses of the micro-emulsion of ethyl 4-biphenylylacetate, ethyl 4-biphenylylacetate and sodium 4-biphenylylacetate are expressed as those of 4-biphenylylacetic acid, and doses of aspirin DL-lysine as those of aspirin.
[b]Dose required to cause a 20% inhibition of adjuvant-injected paw volume against the vehicle control. This value was calculated from the mean % inhibition of swelling combined for measurement intervals indicated.
[c]$p < 0.05$, **$p < 0.01$ A-3: Analgesic Activity (acetic acid stretching method)

(a) Experimental animals: dd-strain male mice (body weight about 18 g), 10 per group.

(b) Test drugs: Micro-emulsions containing 2% (w/v), calculated as 4-biphenylylacetic acid, of methyl 4-biphenylylacetate and ethyl 4-biphenylylacetate respectively (prepared as in Examples 1 and 2) were each diluted with Venolipid to 4, 8, and 16 times, and administered at a dose of 0.1 ml/10 g of body weight. Venolipid ® was used as a vehicle control.

(c) Experimental procedure

Each of the test drugs was administered into the tail vein of each mouse, and 5 minutes later, 0.6% acetic acid (0.1 ml/10 g) was intraperitoneally administered. The number of stretchings for 10 minutes was measured, and the inhibition rate against the vehicle control group was calculated.

(d) Experimental Results

The results are shown in FIG. 1. When acetic acid was intraperitoneally administered after the administration of each test drug into the tail vein of the rat, the 50% inhibition rates ($ED_{50}$) of the micro-emulsion containing methyl 4-biphenylylacetate and ethyl 4-biphenylylacetate were 18 mg/kg and 23 mg/kg respectively. In either case, the analgesic effect was noted.

| the inflamed foot pad. |
| --- |
| 1.5 = Limping with occasional 3-legged gait (paw kept off walking surface) or intermittent use of digits in combination with the inflamed foot pad. |
| 2.0 = Continous 3-Legged gait and/or only the tips of the digits touching the waling surface without using the inflamed foot pad. |

Any rat not showing a gait score of 2 was eliminated from this test. Drugs and vehicles were then administered intravenously. Measurements of the gait were made at 1, 2, 3 and 4 hours after drug administration.

(d) Experimental results:

The micro-emulsions of this invention showed an effect on an abnormal gait of the inflamed paw in doses of 2.5 to 10.0 mg/kg calculated as 4-biphenylylacetic acid, and its $ED_{50}$ value was 4.8 mg/kg calculated as 4-biphenylylacetic acid.

In contrast, sodium 4-biphenylacetate in an ordinary solution form showed an $ED_{50}$ of 7.1 mg/kg/

Accordingly, the effect of the micro-emulsion of this invention was especially superior.

TABLE 5

Effects on reversal of abnormal 3-legged gait in rats

| Test drugs | No. of animals | $ED_{50}^{(a)}$ (mg/kg) |
|---|---|---|
| Sodium 4-biphenylylacetate | 7 | 7.1 |
| Micro-emulsion of ethyl 4-biphenylylacetate (Example 2) | 7 | 4.8 |
| Aspirin-DL.Lysine | 7 | 93.2 |

$^{(a)}$Dose required to cause at least a 50% reversal of gait score of 2($<=1$ score) in 50% of the rats. This value was calculated from the highest effective rate for measurement intervals.

A-5: Effects on body temperature in pyretic rats antipyretic activity (a) Experimental animals SD-strain male rats (120-185 g).

(b) Test drugs: The same as in A-1 [Test 2].

(c) Experimental procedure:

Male Sprague-Dawley rats, weighing 120-185 g, were injected subcutaneously in the nape of the neck with 2 ml of a 20% suspension of dried brewers yeast in physiological saline. Drugs and vehicles were administered intravenously 17 hours after treatment of yeast suspension. Rectal temperature was recorded with a thermistor type thermometer (Natsume Seisakusho, BMA-77 Type) just prior to drug administration and at ½, 1, 2 and 4 hours after drug administration.

(d) Experimental results:

The micro-emulsions of this invention showed a significant antipyretic activity on brewer's yeast-induced fever in doses of 1.25 to 10.0 mg/kg calculated as 4-biphenylylacetic acid. Ethyl or sodium 4-biphenylylacetate in an ordinary solution form also showed a significant antipyretic activity in doses of 2.5 to 10.0 mg/kg, calculated as 4-biphenylylacetic acid.

The $ED_{50}$ of the micro-emulsion of this invention was 1.5 mg/kg, whereas ethyl 4-biphenylylacetate and sodium 4-biphenylylacetate showed an $ED_{50}$ of 3.1 and 2.6 mg/kg.

It is found therefore that the micro-emulsion of this invention has 2 times as good an effect as the ordinary solution forms of ethyl and sodium 4-biphenylylacetates.

TABLE 6

Antipyretic effects

| Test drugs | No. of animals | $ED_{50}^{(a)}$ (mg/kg) |
|---|---|---|
| Micro-emulsion of ethyl 4-biphenylylacetate | 9 | 1.5 |
| Ethyl 4-biphenylylacetate | 10 | 3.1 |
| Sodium 4-biphenylylacetate | 9 | 2.6 |
| Aspirin-DL.Lysine | 9 | 76.3 |

$^{(a)}$Dose required to reduce a body temperature by at least 1.5° C. against the vehicle control in 50% of the rats. This value was calculated from the highest effective rate for measurement intervals.

[B] Distribution to the tissue (a) Experimental animals: Wistar-strain male rats (body weight 60-220 g), 6 per group.

(b) Test drugs:

A micro-emulsion containing 2% (w/v), calculated as 4-biphenylylacetic acid, of methyl 4-biphenylylacetate (prepared as in Example 1) and an aqueous solution of sodium 4-biphenylylacetate as a control drug.

(c) Experimental procedure:

The test drug was administered into the tail vein in a dose of 10 mg/kg, calculated as 4-biphenylylacetic acid. The rats were periodically killed, and the major organs were extracted. The concentration of the drug in the tissues were measured by the conventional HPLC method. The concentration within the tissue was calculated as 4-biphenylylacetic acid.

(d) Experimental results:

The results are shown in FIG. 2. The distribution of the methyl 4-biphenylylacetate and sodium 4-biphenylylacetate to the tissue were examined. At 30 seconds after the administration of the test drugs, both drugs reached concentrations above those at which they showed a pharmacological activity (the action of 4-biphenylylacetic acid to inhibit synthesis of prostaglandin: $IC_{50}$ 0.68 ng/ml (see E. L. Tolman, American Cyanamid Company's Reprot). It is seen that in the spleen and in the muscles, the micro-emulsion containing methyl 4-biphenylylaceate was distributed in a concentration 2.5 to 3 times as high as sodium 4-biphenylylacetate. This suggests that micro-emulsion containing methyl 4-biphenylylacetate transfers to the tissues within a shorter period of time, and its effect in a lesser dose is expected. Ethyl 4-biphenylylacetate showed the same transferability to the tissues, and exhibits an excellent effect.

[C] Toxicity test

Charles River-strain SD male rats (6 weeks old; body weight 160-170 g), 5 per group, were used. A micro-emulsion containing 2% (w/v), calculated as 4-biphenylylacetic acid, of methyl 4-biphenylylacetate or ethyl 4-biphenylylacetate (prepared in accordance with Example 1 or 2 given hereinbelow) was administered once into the tail vein. The animals were observed for 3 days to perform a toxicity test. The doses were 50, 100, 200 and 400 mg/kg. As a control, an aqueous solution of sodium 4-biphenylylacetate was administered. The results are shown in Table 7.

From the results no change ascribable to the drugs was noted in the observations of general symptoms and the results of autopsy when the micro-emulsions containing methyl 4-biphenylylacetate and ethyl 4-biphenylylacetate were administered in doses of up to 100 mg/kg. On the other hand, with the control sodium 4-biphenylylacetate, no change in general symptoms and the results of autopsy was noted in administration in doses of up to 50 mg/kg. But changes occurred in administration of more than 100 mg/kg. Accordingly, it is evident that the micro-emulsion of this ivnention is safer than sodium 4-biphenylylacetate in the ordinary solution form.

TABLE 7

| Drug | Dose (a) (mg/kg) | Amount administered (ml/kg) | Toxicity Test Number of the dead | Findings General symptoms | Autopsy |
|---|---|---|---|---|---|
| Solvent control group | 0 | 20 | 0/5 | No change | No change |
| Micro-emulsion containing methyl | 50 | 2.5 | 0/5 | No change | No change |
|  | 100 | 5 | 0/5 |  |  |

TABLE 7-continued

| | | | Toxicity Test | | |
|---|---|---|---|---|---|
| | | Amount | Number | Findings | |
| | Dose (a) | administered | of the | | |
| Drug | (mg/kg) | (ml/kg) | dead | General symptoms | Autopsy |
| 4-biphenylyl-acetate (2%, w/v) (Example 1) | 200 400 | 10 20 | 0/5 1/5 | Body weight increase inhibition (at least 200 mg/kg), spontaneous motion decreased (400 mg/kg), pallor (400 mg/kg) | Peptic ulcer occurred (at least 200 mg/kg), fibrinogenous intestinal adherence (at least 200 mg/kg) |
| Micro-emulsion containing ethyl 4-biphenylyl-acetate (2%, w/v) (Example 2) | 50 100 200 400 | 2.5 5 10 20 | 0/5 0/5 0/5 1/5 | No change<br><br>Body weight increase inhibition (at least 200 mg/kg), spontaneous motion decreased (400 mg/kg), pallor (400 mg/kg) | No change<br><br>Peptic ulcer occurred (at least 200 mg/kg), fibrinogenous intestinal adherence (at least 200 mg/kg) |
| Sodium 4-biphenylyl-acetate | 50 100 200 400 | 2.5 5 10 20 | 0/5 0/5 3/5 3/5 | No change<br>Body weight increase inhibition (at least 100 mg/kg), spontaneous motion decreased (100 mg/kg), tarry feces (200 mg/kg), pallor (at least 200 mg/kg) | No change<br>Peptic ulcer occurred (at least 100 mg/kg), fibrinogenous intestinal adherence (at least 100 mg/kg) |

(a) Calculated as 4-biphenylylacetic acid.

[D] Stability test:
The micro-emulsions containing the 4-biphenylacetic acid ester provided by this invention were tested for 6 months for stability. The content was measured by high-performance liquid chromatography (device: 655-15 made by Hitachi Limited), and the particle size was measured by a light-transmission type particle size distribution analyzer (CAPA-500, made by Horiba Limited). The results are shown in Table 8. In a stability test at room temperature (25° C.) for 6 months, no change was observed in content, appearance, pH and particle diameter. Accordingly, the micro-emulsion of this invention is very stable pharmaceutically.

TABLE 8

| | | Stability Test | | | |
|---|---|---|---|---|---|
| | | Period of observation | | | |
| Micro-emulsion | Test items | Immediately after preparation | 1 month | 3 months | 6 months |
| Example 1 | Content (mg/ml) (residual rate, %) | 22.08 (100.0) | 22.30 (101.0) | 21.86 (99.0) | 21.86 (99.0) |
| | Appearance | White non-transparent emulsion | — | — | — |
| | pH | 6.80 | 6.62 | 6.73 | 6.63 |
| | Mean particle diameter ($\mu$m) | 0.15 | 0.16 | 0.17 | 0.16 |
| Example 2 | Content (mg/ml) (residual rate, %) | 23.12 (100.0) | 23.06 (99.7) | 23.20 (100.3) | 23.00 (99.5) |
| | Appearance | White non-transparent emulsion | — | — | — |
| | pH | 6.65 | 6.58 | 6.54 | 6.50 |
| | Mean particle diameter ($\mu$m) | 0.15 | 0.16 | 0.17 | 0.15 |
| Example 3 | Content (mg/ml) (residual rate, %) | 21.20 (100.0) | 21.14 (99.7) | 21.24 (100.2) | 21.14 (99.7) |
| | Appearance | White non-transparent emulsion | — | — | — |
| | pH | 6.42 | 6.38 | 6.36 | 6.34 |
| | Mean particle diameter ($\mu$m) | 0.16 | 0.17 | 0.16 | 0.14 |
| Example 15 | Content (mg/ml) (residual rate, %) | 32.15 (100.0) | 31.61 (98.3) | 31.53 (98.1) | 31.84 (99.0) |
| | Appearance | White non-transparent emulsion | — | — | — |
| | pH | 6.81 | 6.69 | 6.89 | 6.78 |
| | Mean particle diameter ($\mu$m) | 0.12 | 0.12 | 0.12 | 0.12 |
| Example 16 | Content (mg/ml) (residual rate, %) | 46.80 (100.0) | 47.03 (100.5) | 46.41 (99.2) | 46.40 (99.1) |
| | Appearance | White non-transparent emulsion | — | — | — |
| | pH | 6.81 | 6.91 | 6.80 | 6.93 |
| | Mean particle diameter ($\mu$m) | 0.13 | 0.13 | 0.13 | 0.13 |

[E] Clinical tests
(a) Test drugs:
Lipo BPAA: Micro-emulsion containing ethyl 4-biphenylylacetate prepared in Example 2; administered once in a dose of 40 mg/2 ml, calculated as 4-biphenylylacetic acid, by intravenous injection.

Decadron ®: sodium dexamethasone phosphate, a steroidal anti-inflammatory drug produced by Merck- Banyu Company, administered once in a dose of 4 mg/1 ml Venopyrin ®: aspirin DL-lysine, a salicylate-type preparation made by Green Cross Company; 900 mg (b) Method of Evaluation:

Self-evaluation by patients in accordance with 10-step numerical scale for pain degree 10: severest pain
5: moderate pain
0: no pain (c) Experimental results FIG. 3 shows the 10 step scales of the analgesic effects of the micro-emulsion of this invention (Lipo BPAA) and Decadron in patients with neuralgia. FIG. 4 shows the 10 step scales of the analgesic effects of Lipo BPAA and Decadron on patients with calculosis. FIG. 5 shows the 10-step scales of lipo BPAA and Venopirine ® as the degree of alleviation of pain in patients with chronic rheumatoid arthritis.

Figure 6:
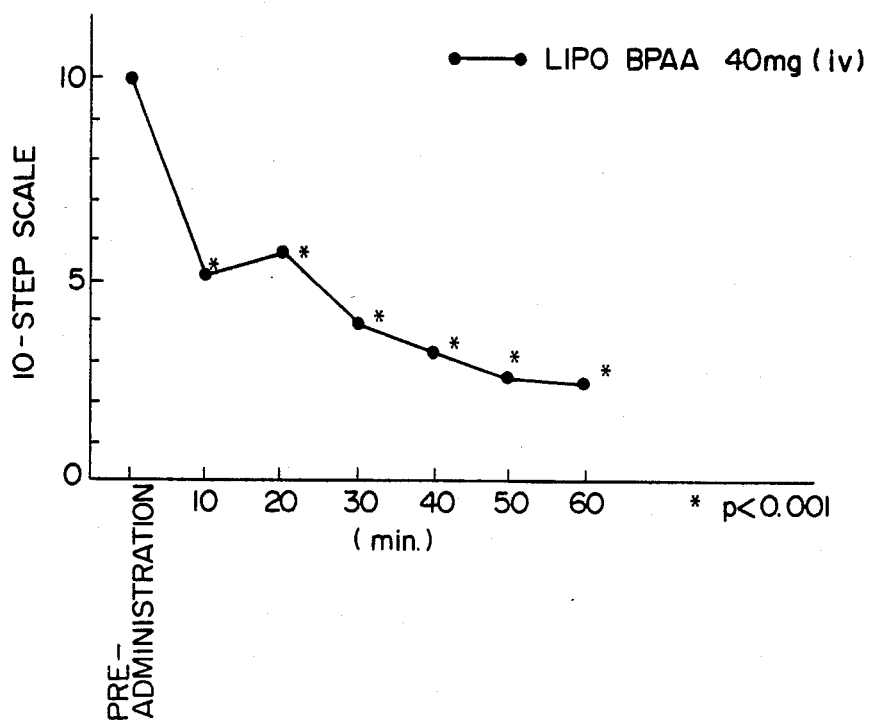
Figure 7:
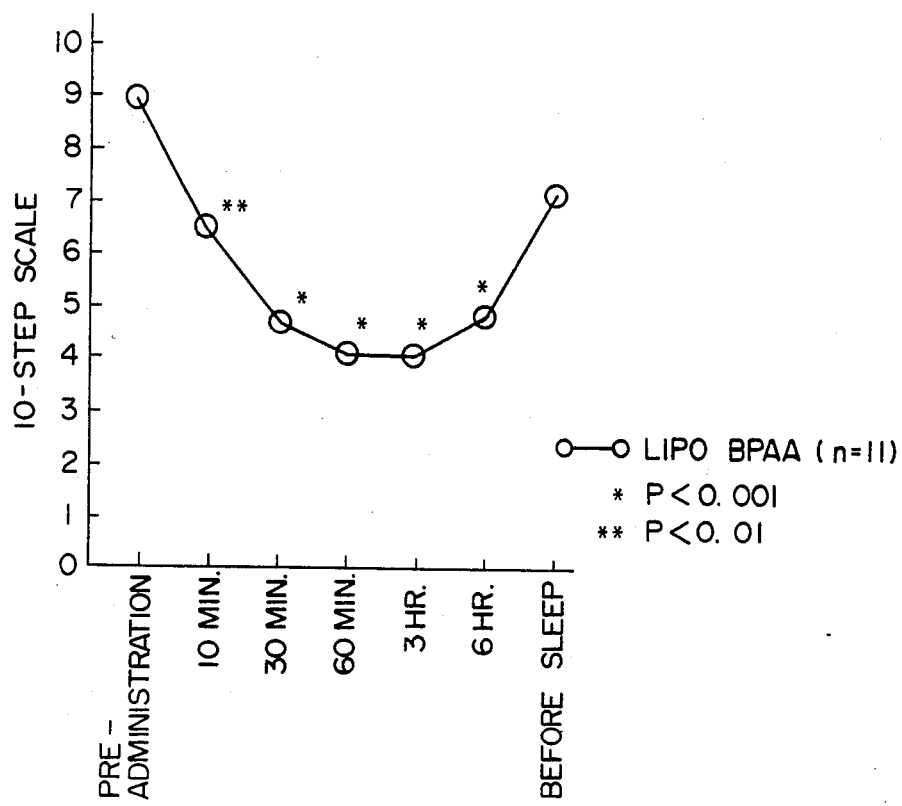

FIGS. 6 and 7 showed the 10-step scales of Lipo BPAA as the degree of allevation of pain in patiens with acute upper repiratory tract inflammation and patients with cancerous pain.

As is clear from the results shown in FIGS. 3 to 7, the micro-emulsion of this invention had a marked effect on urolithic pain and neuralgia on which steroidal agents show little or no effect, and showed higher effectiveness on chronic rheumatoid arthritis than Venopyrin ®. It also showed a marked effect on pharyngalgia of a patient with acute upper respiratory tract inflammation. The analgesic effect of the micro-emulsion of this invention is characterized by its rapid manifestation and durability. Particularly, sialolithiasis pain was completely removed in 10 to 20 minutes after injection.

The micro-emulsion of this invention showed no side effects.

As stated above, the micro-emulsion of this invention containing the 4-biphenylylacetic acid ester has excellent distribution (incopopration to a site of inflammation with reduced side effects and toxicity). The pharmacological effect of the active ingredient of the micro-emulsion is exhibited effectively and strongly over an extended period of time. Furthermore, since the micron-emulsion is stable, it is very useful clinically as a liquid injectable preparation for anti-inflammatory, analgesic and antipyretic purposes.

Injection (parenteral, e.g., intravenous, intra-articular, etc.), eye-dropping, etc. can be cited as routes of administration of this micro-emulsion. The dosage varies according to the administration route, prescription, patient's symptoms, etc., but a usual dose for adults is 5 mg to 50 mg (as 4-biphenylylacetic acid) each time, once to three times a day. This dosage, of course, can be exceeded according to the severity of the condition, body weight, sex and type of disease of a patient, the physician's judgement, etc. The administration of this emulsion brings about a marked improvement in rheumatoid arthritis, osteoarthritis, lumbago, frozen shoulder, neck/shoulder/arm syndrome, postoperative and traumatic inflammation and pain, cancerous pain, herpes zoster, gout attack, tendinitis/tenosynovitis, neuralgia, myalgia, pain after tooth extraction, conjunctivitis, ueveitis, etc.

The following Examples illustrate the present invention more specifically.

EXAMPLE 1

4.28 g (corresponding to 4.0 g of 4-biphenylylacetic acid) of methyl 4-biphenylylacetate was added to 20 g of soybean oil described in Japanese Pharmacopoeia, and the mixture was dissolved under heat. Then, 2.4 g of purified soybean phospholipid and 5 g of glycerol were added to the solution, and the mixture was vigorously stirred under heat. A suitable amount of distilled water was added, and the mixture was stirred by a polytron homogenizer to prepare a crude emulsion. The crude emulsion was emulsifierd under high pressure by a Gaulin high-energy type homogenizer, and distilled water was added to adjust the amount of the emulsion to 200 ml. There was obtained a micro-emulsion containing methyl 4-biphenylylacetate. The dispersed lipid particles had a mean particle diameter of 0.15 micron, and it did not contain particles having a size of at least 1 micron.

EXAMPLE 2

Example 1 was repeated except that 4.52 g of ethyl 4-biphenylylacetate was used instead of 4.28 g of methyl 4-biphenylylacetate. Thus, a micro-emulsion containing ethyl 4-biphenylylacetate was obtained.

The dispersed lipid particles in the micro-emulsion had a mean particle diameter of 0.15 micron, and it did not contain particles having a size of at least 1 micron.

EXAMPLE 3

Example 1 was repeated except that purified yolk phospholipid was used instead of the purified soybean phospholipid. A micro-emulsion containing methyl 4-biphenylylacetate was obtained.

EXAMPLE 4

Ethyl 4-biphenylylacetate (0.43 g corresponding to 0.4 g of 4-biphenylylacetic acid) was added to 20 g of soybean oil described in the Japanese Pharmacopoeia, and the mixture was heated to form a solution. To the solution were added 2.0 g of Pluronic F-68 ® (a polyoxyethylene/polyoxypropylene ether-type nonionic surface-active agent made by Asahi-Denka Kogyo K. K.) and a suitable amount of distilled water. The mixture was stirred by a polytron homogenizer to preapre a crude emulsion. The crude emulsion was emulsified under high pressure by a Gaulin high-energy homogenizer, and distilled water was added to make 200 ml. A micro-emulsion containing ethyl 4-biphenylylacetate was obtained. The dispersed lipid particles in the micro-emulsion had a mean diameter of 0.15 micron, and it did not contain particles having a size of at least 1 micron.

EXAMPLE 5

Ethyl 4-biphenylylacetate (0.43 g) was added to 10 g of soybean oil described in the Japanese Pharmacopoeia and 10 g of MCT, and dissolved under heat. Purified soybean phospholipid (1.2 g), 1.2 g of purified yolk phospholipid and 5 g of glycerol were added, and the mixture was vigorously stirred under heat. After dissolving, a suitable amount of water was added, and the mixture was stirred by a polytron homogenizer to form a crude emulsion. The crude emulsion was emulsified under high pressure by a Gaulin high-energy homogenizer. Distilled water was added to make 200 ml. A micro-emulsion containing ethyl 4-biphenylylacetate as obtained. The dispersed lipid particles in the micro-emulsion had a mean particle diameter of 0.15 micron, and it did not contain particles having a size of at least 1 micron.

EXAMPLE 6

Example 1 was repeated except that the amounts of soybean oil, methyl 4-biphenylylacetate, purified soybean phospholipid, and glycerin were changed to 100 g, 53.5 g, 7.5 g and 12.5 g, respectively. There was obtained 250 ml of a micro-emulsion containing methyl 4-biphenylylacetate in a high concentration. The dispersed lipid particles in the micro-emulsion had a mean particle diameter of 0.15 micron, and it did not contain particles having a size of at least 1 micron.

EXAMPLE 7

Ethyl 4-biphenylylacetate (0.43 g) was dissolved in 20 g of soybean oil described in the Japanese Pharmacopoeia under heat. To the solution were added 2.4 g of purified soybean phospholipid, 0.6 g of cholesterol and 5 g of glycerol, and the mixture was vigorously stirred under heat. A suitable amount of distilled water was added, and the mixture was stirred by a Polytoron homogenizer to prepare a crude emulsion and then emulsified under high pressure by a Gaulin high-energy homogenizer. Distilled water was added to make 200 ml. A micro-emulsion containing ethyl 4-biphenylylacetate was obtained. The dispersed lipid particles in the micro-emulsion had a mean particle size of 0.14 micron, and it did not contain particles having a size of at least 1 micron.

EXAMPLE 8

Example 7 was repeated except that 0.04 g of sodium palmitate was added instead of 0.6 g of cholesterol. A micro-emulsion containing ethyl 4-biphenylylacetate was obtained.

EXAMPLE 9

Example 7 was repeated except that 0.4 g of 0-palmitoyl dextran (molecular weight 40000) was added instead of 0.6 g of cholesterol. A micro-emulsion containing ethyl 4-biphenylylacetate was obtained.

EXAMPLE 10

Albumin (5 g) was added to the micro-emulsion obtained in Example 1, and the mixture was lyophilized to obtain a powder of a micro-emulsion of containing ethyl 4-biphenylylacetate.

EXAMPLE 11

Ethyl 4-biphenylylacetate (0.2825 g corresponding to 0.25 g of 4-biphenylylacetic acid) was added to 100 g of soybean oil described in the Japanese Pharmacopoeia, and dissolved under heat. To the solution were added 24 g of purified soybean phospholipid and 50 g of glycerol, and the mixture was vigorously sirred under heat. A suitable amount of distilled water was added to the solution, and the mixture was stirred by a polytron homogenizer to prepare a crude emulsion.

The crude emulsion was then emulsified under high pressure by a Gaulin high-energy homogenizer, and distilled water was added to make 1000 ml. A micro-emulsion containing ethyl 4-biphynylylacetate was obtained. The dispersed particles in the micro-emulsion had a mean particle diameter of 0.16 micron, and it did not contain particles with a particle diameter of at least 1 micron.

EXAMPLE 12

Example 11 was repeated except that the amount of ethyl 4-biphenylylacetate was changed to 0.565 g. A micro-emulsion containing ethyl 4-biphenylylacetate was obtained. The dispersed lipid particles in the micro-emulsion had a mean particle diameter of 0.18 micron, and it did not contain particles having a size of at least 1 micron.

EXAMPLE 13

Example 11 was repeated except that the amount of ethyl 4-biphenylylacetate was changed to 1.13 g. A micro-emulsion containing ethyl 4-biphenylylacetate was prepared. The dispersed lipid particles in the micro-emulsion had a mean particle diameter of 0.14 micron, and it did not contain particles having a size of at least 1 micron.

EXAMPLE 14

Example 11 was repeated except that the amount of ethyl 4-biphenylylacetate was changed to 2.26 g. A micro-emulsion containing ethyl 4-biphenylylacetate was obtained. The dispersed particles in the micro-emulsion had a mean particle diameter of 0.13 micron, and it did not containing particles having a size of at least 1 micron.

EXAMPLE 15

Example 11 was repeated except that the amount of ethyl 4-biphenylylacetate was changed to 33.9 g. A micro-emulsion containing ethyl 4-biphenylylacetate was obtained. The dispersed particles in the micro-emulsion had an average particle diameter of 0.13 micron, and it did not containing particles having a size of at least 1 micron.

EXAMPLE 16

Example 11 was repeated except that the amount of ethyl 4-biphenylylacetate was changed to 45.2 g. A micro-emulsion containing ethyl 4-biphenylylacetate was obtained. The dispersed particles in the micro-emulsion had a mean particle diameter of 0.13 micron, and it did not containing particles having a size of at least 1 micron.

What we claim is:

1. A method for treating inflammation, pain and/or fever in a mammal, which comprises parenterally administering to the mammal a pharmaceutical oil-in-water type micro-emulsion comprising fine particles of a vegetable oil or triglyceride of a medium-chain fatty acid having 8 to 12 carbon atoms containing an effective amount of a 4-biphenylylacetic acid ester of the formula

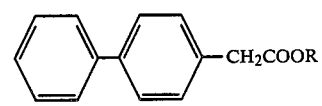

(I)

wherein R represents an alkyl group, an aqueous medium and 0.05 to 25% (w/v) of a physiologically acceptable phospholipid for dispersing said fine particles in said aqueous medium.

2. The method of claim 1 wherein the 4-biphenylylacetic acid ester is ethyl 4-biphenylylacetate.

3. The method of claim 1 the micro-emulsion is administered intravenously or intra-articularly.

4. The method of claim 1 wherein the micro-emulsion consists essentially of 5 to 50% (w/v) of fine particles of a vegetable oil or triglyceride of a medium-chain fatty acid having 8 to 12 carbon atoms containing 0.01 to 10% (w/v) of the 4-biphenylylacetic acid ester, 0.05 to 25% (w/v) of the physiologically acceptable phospholipid, an isotonizing agent selected from the group consisting of glycerol, sugar alcohols, monosaccharides, disaccharides and amino acids in an amount sufficient to isotonize the emulsion, and water.

5. The method of claim 4 wherein the micro-emulsion consists essentially of 5 to 30% (w/v) of fine particles of soybean oil having dissolved therein 1 to 5% (w/v) of ethyl 4-biphenylylacetate, 0.5 to 25% (w/v) of purified soybean oil phospholipid, 1 to 5% (w/v) of glycerol, and the remainder being water.

6. The method of claim 5 wherein the purified soybean oil phospholipid has a phosphatidyl choline content of at least 80% and an iodine value of 35 to 45.

7. A pharmaceutical oil-in-water type micro-emulsion comprising fine particles of a vegetable oil or a triglyceride of a medium-chain fatty acid having 8 to 12 carbon atoms containing 0.01 to 10% (w/v) of a 4-biphenylylacetic acid ester of the formula

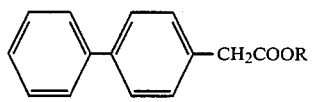

(I)

wherein R represents an alkyl group, an aqueous medium, and 0.05 to 25% (w/v) of a physiologically acceptable phospholipid for dispersing said fine particles in said aqueous medium.

8. The micro-emulsion of claim 7 which further contains an isotonizing agent selected from the group consisting of glycerol, sugar alcohols, monosaccharides, disaccharides and amino acids.

9. The micro-emulsion of claim 8 wherein the 4-biphenylylacetic acid ester is ethyl 4-biphenylylacetate.

10. The micro-emulsion of claim 8 wherein the vegetable oil is pharmaceutically acceptable soybean oil.

11. The micro-emulsion of claim 5 wherein the physiologically acceptable phospholipid is a purified vegetable oil phospholipid.

12. The micro-emulsion of claim 6 wherein the purified vegetable oil phospholipid is purified soybean oil phospholipid.

13. The micro-emulsion of claim 7 which consists essentially of 5 to 50% (w/v) of fine particles of a vegetable oil or triglyceride of a medium-chain fatty acid having 8 to 12 carbon atoms containing 0.01 to 10% (w/v) of the 4-biphenylylacetic acid ester, 0.05 to 25% (w/v) of the physiologically acceptable phospholipid, an isotonizing agent selected from the group consisting of glycerol, sugar alcohols, monosaccharides, disaccharides and amino acids in an amount sufficient to isotonize the emulsion, and water.

14. The micro-emulsion of claim 13 wherein the 4-biphenylylacetic acid ester is ethyl 4-biphenylylacetate.

15. The micro-emulsion of claim 1 which consists essentially of 5 to 30% (w/v) of fine paritcles of soybean oil having dissolved therein 1 to 5% (w/v) of ethyl 4-biphenylylacetate, 0.5 to 25% (w/v) of a purified soybean oil phospholipid, 1 to 5% (w/v) of glycerol, and the remainder being water.

16. The micro-emulsion of claim 1 wherein the fine particles of the oil or fat have a mean particle diameter of not more than 1 micron, preferably not more than 0.3 micron.

17. The micro-emulsion of claim 12 wherein the purified soybean oil phospholipid has a phosphatidyl choline content of at least 80% and an iodine value of 35 to 45.

* * * * *